United States Patent [19]

Louvet et al.

[11] Patent Number: 5,286,475

[45] Date of Patent: Feb. 15, 1994

[54] ANHYDROUS COSMETIC COMPOSITION IN THE AEROSOL FORM FORMING A FOAM

[75] Inventors: Nathalie Louvet, L'hay Les Roses; Liliane Lukassen, Chevilly Larue; Jean P. Yquel, Colombes, all of France

[73] Assignee: L'oreal, Paris, France

[21] Appl. No.: 789,828

[22] Filed: Nov. 8, 1991

[51] Int. Cl.$^5$ .............................. A61K 9/12
[52] U.S. Cl. .................... 424/45; 514/945; 424/47
[58] Field of Search .............. 424/45, 43; 514/945

[56] References Cited

U.S. PATENT DOCUMENTS

| | | | |
|---|---|---|---|
| 3,419,658 | 12/1968 | Sanders | 424/45 |
| 3,770,648 | 11/1973 | Mackles | 252/305 |
| 4,016,287 | 4/1977 | Eberhardt et al. | 514/629 |
| 4,889,709 | 12/1989 | Mackles et al. | 424/45 |

FOREIGN PATENT DOCUMENTS

| | | |
|---|---|---|
| 2157784 | 6/1973 | France . |
| 2192795 | 2/1974 | France . |

OTHER PUBLICATIONS

CA 94(26):214393v.
CA 87(12):90600u.

*Primary Examiner*—Thurman K. Page
*Assistant Examiner*—Raj Bawa
*Attorney, Agent, or Firm*—Oliff & Berridge

[57] ABSTRACT

An anhydrous cosmetic composition in the aerosol form for forming a foam is composed of a propellant and an oily phase. The oily phase contains in combination at least one cosmetic oil or a mixture of an oil and a fatty substance and at least one foaming agent. The foaming agent corresponds to the following general formula:

$$R_1-O-\underset{\underset{O}{\|}}{C}-NH-(CH_2)_{10}-\underset{\underset{O}{\|}}{C}-OR$$

wherein
  R represents a hydrogen atom or an alkyl radical having 14 to 20 carbon atoms, and
  $R_1$ represents an alkyl radical having 8 to 18 carbon atoms. This composition allows a highly stable foam to be obtained.

10 Claims, No Drawings

ANHYDROUS COSMETIC COMPOSITION IN THE AEROSOL FORM FORMING A FOAM

TECHNICAL FIELD

The present invention relates to an anhydrous cosmetic composition in the aerosol form for forming a foam, the latter being intended particularly for the removal of face and eye makeup, for skin care, particularly of dry skin, or for hair treatment.

BACKGROUND

The principal problem encountered in the preparation of foam forming aerosol compositions resides essentially in the fact that, once formed, the foam must have good stability for a certain period of time.

It is also appropriate for the foam to be sufficiently stiff and oily when applied.

French Patent No. 2,157,784 describes an anhydrous aerosol composition containing a foaming agent, a foaming organic liquid, a silicone resin, and a propellant. The goal of this patent is to obtain a foam which is stable but which "breaks easily," and the addition of silicones allows this to be achieved.

SUMMARY OF THE INVENTION

The present invention provides anhydrous compositions in aerosol form for forming a foam whose foam quality simultaneously has good stability, firmness, and oiliness characteristics.

After a number of studies, it has unexpectedly and surprisingly been found that a certain class of compounds derived from N-carboalkyloxy-11-aminoundecanoic acids or their esters constitute excellent foaming agents for compositions in the aerosol form. By using these compounds, it is possible to obtain foams with excellent stability over time as well as very good cosmetic properties, particularly of oiliness.

Because of this improved stability, the products are easy to apply and have a pleasant consistency when used.

DETAILED DESCRIPTION OF PREFERRED EMBODIMENTS

The present invention, as a novel industrial product, comprises an anhydrous cosmetic composition in aerosol form for forming a foam. The composition is composed of a propellant and an oily phase containing, in combination, at least one cosmetic oil or a mixture of an oil and a fatty substance and at least one foaming agent, said foaming agent having the following general formula:

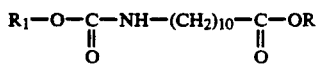  (I)

wherein
R represents a hydrogen atom or an alkyl radical having 14 to 20 carbon atoms, and
$R_1$ represents an alkyl radical having 8 to 18 carbon atoms.

According to one particular embodiment, radical R preferably represents an alkyl radical having 16 to 18 carbon atoms and radical $R_1$ represents an alkyl radical having 10 to 16 carbon atoms.

Among the alkyl radicals having 14 to 20 carbon atoms, the following examples may be cited in particular: tetradecyl, hexadecyl, and octadecyl, the hexadecyl radical being particularly preferred.

Of the alkyl radicals with 8 to 18 carbon atoms, the following examples may be cited: octyl, decyl, dodecyl, tetradecyl, hexadecyl, 2-hexyldecyl, and isostearyl, the decyl and hexadecyl radicals being particularly preferred.

Of the foaming agents with general formula (I) above, the following examples may be cited in particular:
N-carbohexadecyloxy-11-aminoundecanoic acid
N-carbodecyloxy-11-aminoundecanoic acid
hexadecyl N-carbohexadecyloxy-11-aminoundecanoate
octadecyl N-carbohexadecyloxy-11-aminoundecanoate, and
hexadecyl N-carbodecyloxy-11-aminoundecanoate.

Most of the N-carboalkyloxy-11-aminoundecanoic acids are known, whereas their esters are novel.

Various methods may be employed to obtain them; one comprises reacting a fatty alcohol ($R_1OH$) with an isocyanate of the formula:

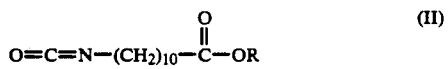  (II)

R and $R_1$ having the same meanings as given above for formula (I).

Another method that can be used comprises reacting a chloroformate with formula $R_1OCOCl$ or an imidazolide with the formula:

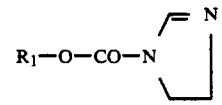

with an amine with the formula:

  (III)

where R and $R_1$ have the same meanings as given above.

These two methods, whose objective is the formation of the carbamate function, may be implemented by conventional methods such as those described in "Advanced Organic Chemistry," Third Edition, Ed. Jerry, March 1985.

The reactions are generally carried out in an organic and/or aqueous solvent medium in the presence of a base, preferably sodium hydroxide, potassium hydroxide, or triethylamine.

These methods can also be employed starting with the acids of compounds (II) and (III) (R=H), in which case the esters are produced by classical methods, particularly by esterification in the presence of the selected alcohol, which may or may not be in excess, and an acid catalyst such as sulfuric acid or p-toluenesulfonic acid, possibly in an organic solvent, preferably an aromatic solvent such as toluene.

From the salts of these acids, it is also possible to produce esters by classical methods, in particular by substitution with alkyl halides or sulfates, in an organic solvent medium or by phase transfer.

The esters may also be obtained by transesterification from the corresponding methyl and ethyl esters and the desired alcohol.

As mentioned above, the anhydrous cosmetic compositions according to the invention contain at least one oil or a mixture of at least one oil and one fatty substance.

The oils that can be used in the compositions according to the invention are of plant, animal, mineral, or synthetic origin, of which the following examples may be cited in particular:

mineral oils such as paraffin oil, liquid paraffin, and mineral oils with a boiling point between 310° and 410° C.;

oils of animal origin such as perhydrosqualene, pig oil, caballine oil, and tortoise oil;

plant oils such as sweet-almond oil, calophyllum oil, palm oil, avocado oil, jojoba oil, sesame oil, sunflower seed oil, karite oil, safflower oil, copra oil, olive oil, castor oil, and grain germ oils such as wheat germ oil;

silicone oils such as polydimethylsiloxane;

synthetic esters such as Purcelin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, propylene glycol dicaprylate, and diisopropyl adipate;

organic alcohols such as oleic alcohol, linoleic alcohol, linolenic alcohol, isostearyl alcohol, 2-octyldodecanol, and isocetyl alcohol; and esters derived from lanolic acid such as isopropyl lanolate and isocetyl lanolate.

The following examples may also be cited: acetylglycerides, octanoates and decanoates of alcohols and polyalcohols such as those of glycol and glycerol, ricinoleates of alcohols and polyalcohols such as that of cetyl alcohol.

Of the fatty substances that can be used in a mixture with at least one oil, the following examples may be mentioned in particular:

mineral waxes such as microcrystalline waxes, paraffin, petrolatum, and vaseline;

fossil waxes such as alkerite and montan wax;

waxes of animal origin such as beeswax, spermaceti, lanolin wax, lanolin derivatives such as lanolin alcohols, hydrogenated lanolin, hydroxylated lanolin, acetylated lanolin, lanolin fatty acids, and acetylated lanolin alcohol;

waxes of plant origin such as candelilla wax, carnauba wax, Japan wax, and cocoa butter;

hydrogenated oils solid at 25° C. such as hydrogenated castor oil, hydrogenated palm oil, hydrogenated tallow, and hydrogenated cocoa oil;

synthetic waxes such as polyethylene waxes and copolymerized polyethylene waxes;

fatty esters solid at 25° C. such as propylene glycol monomyristate and myristyl myristate; and silicone waxes such as poly(dimethylsiloxy)stearoxysiloxane.

Among the waxes, the following may also be cited: cetyl alcohol, stearyl alcohol, mono-, di-, and triglycerides solid at 25° C., stearic monoethanolamide, rosin and its derivatives such as abietates of glycol and glycerol, sucroglycerides and calcium, magnesium, zinc, and aluminum oleates, myristates, lanolates, stearates and dihydroxystearates.

According to the invention, the anhydrous cosmetic composition contains 20 to 99.95 wt.%, preferably 25 to 85 wt.%, of at least one oil or mixture of an oil and a fatty substance, relative to the total weight of the oily phase.

The concentration of Formula (I) foaming agent is generally between 0.05 and 20 wt. % and preferably between 0.2 and 5 wt.% relative to the weight of the oily phase.

If it is desirable for the foam, after application, to be eliminatable simply by rinsing with water, the composition must then preferably contain one or more oil-soluble surfactants in a concentration of preferably between 5 and 60 wt.% relative to the weight of the oily phase.

Preferably, the surfactant is of the nonionic type and, of these, one may cite as examples the polyol and sugar esters, condensation products of ethylene oxide on fatty acids, on fatty alcohols, on long-chain alkylphenols, on long-chain amides, on sorbitan esters, or on polyglycerol fatty alcohols or on lecithins.

Of these surfactants, those particularly preferred include: sorbitan oleate, sorbitan trioleate, sorbitan tetraoleate, sorbitan oleate ethoxylated with 40 moles of ethylene oxide, sorbitan trioleate ethoxylated with 20 moles of ethylene oxide, and soy lecithin.

The oily phase may also contain various oil-soluble cosmetic ingredients chosen from vitamins, plant or animal extracts, preservatives, fragrances, etc.

This oily phase is pressurized with the aid of a propellant representing 1 to 20 wt.% relative to the total weight of the aerosol composition, preferably 3 to 15%.

Of the propellants usable in the aerosol compositions according to the invention, one may mention in particular as examples: carbon dioxide, nitrous oxide, compressed air, nitrogen, liquefiable aliphatic hydrocarbons such as propane and butanes, including isobutane, pentane, isopentane, neopentane and their mixtures. One may also use halogenated hydrocarbons such as 1,1-difluoroethane, dichlorotetrafluoroethane, dichlorodifluoromethane, monochlorodifluoroethane, and monochlorodifluoromethane as well as their mixtures, and in particular a 40:60 mixture of dichlorotetrafluoroethane and dichlorodifluoromethane as well as a 60:40 mixture of monochlorodifluoroethane and monochlorodifluoromethane.

The proportion of propellant used is not critical but it determines the density of the foam produced. The higher the proportion of propellant, the lower the density of the foam. In general, foam densities are in the range of approximately 0.02 to approximately 0.20 g/cm$^3$ and preferably approximately 0.05 to approximately 0.15 g/cm$^3$.

COMPARATIVE STUDIES

In order to demonstrate the properties of compounds with general formula (I) as foaming agents of compositions according to the invention, a comparison has been made between compounds A, B, and C corresponding to general formula j(I) and the reference compound D to G below, as far as both density of the foam after expansion in air and the stability of the foam over time are concerned.

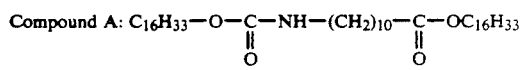

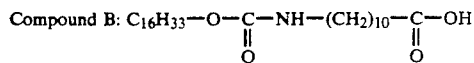

-continued

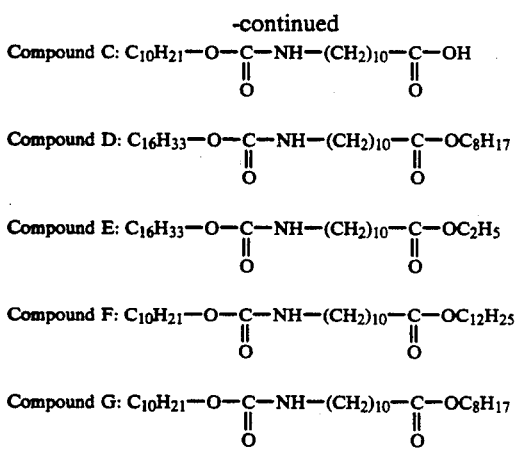

Compound C: $C_{10}H_{21}-O-\underset{\underset{O}{\|}}{C}-NH-(CH_2)_{10}-\underset{\underset{O}{\|}}{C}-OH$ Compound D: $C_{16}H_{33}-O-\underset{\underset{O}{\|}}{C}-NH-(CH_2)_{10}-\underset{\underset{O}{\|}}{C}-OC_8H_{17}$ Compound E: $C_{16}H_{33}-O-\underset{\underset{O}{\|}}{C}-NH-(CH_2)_{10}-\underset{\underset{O}{\|}}{C}-OC_2H_5$ Compound F: $C_{10}H_{21}-O-\underset{\underset{O}{\|}}{C}-NH-(CH_2)_{10}-\underset{\underset{O}{\|}}{C}-OC_{12}H_{25}$ Compound G: $C_{10}H_{21}-O-\underset{\underset{O}{\|}}{C}-NH-(CH_2)_{10}-\underset{\underset{O}{\|}}{C}-OC_8H_{17}$ From each of the above compounds, an aerosol composition with the following composition was prepared:

| Compound to be studied: | 1.5% |
|---|---|
| 2-Octyldodecanol | 20.0% |
| Isopropyl myristate | 20.0% |
| Sorbitan trioleate ethoxylated with 20 moles of ethylene oxide | 4.0% |
| Sorbitan oleate ethoxylated with 40 moles of ethylene oxide | 3.0% |
| Fragrance | 0.3% |
| Liquid paraffin | 51.2% |

Forty-seven grams of the composition obtained are placed in a one-piece aluminum aerosol container. Then, when the container has been closed with a valve fitted with a plunger tube it is pressurized with 3 g of 1,1-difluoroethane.

Test Protocol

The compound studied must produce a foam having a density, after expansion in air from an aerosol device, of less than or equal to 0.3 g/cm$^3$ at 20° C., and must have a stability greater than 30 seconds and more advantageously greater than or equal to 3 minutes.

The density of the foam is measured by the following method: 24 hours after pressurization of the aerosols in a room with a temperature controlled to 20° C.±1° C., a cylindrical cup graduated heightwise (in 10 graduations) which has previously been weighed under vacuum (let its weight be $P_1$) is filled with the foam produced by each aerosol. Each aerosol can is shaken vigorously before use to emulsify the propellant gas thoroughly.

For uniform distribution of the foam in the cup, the aerosol cans are used with a regular, rotating movement.

As soon as the foam has finished expanding, the foam brimming over the cup is immediately and rapidly skimmed off with a broad spatula and the cup is re-weighed (let its weight be $P_2$).

The density of the foam is then determined by the following formula:

$$\text{Density at 20° C.} = \frac{P_2 - P_1}{V}$$

where V is the volume of the cup.

For each aerosol can, three density determinations are made and the value obtained is the mean of these three determinations (in g/cm$^3$).

At regular time intervals, the subsidence of the foam is noted by the number of graduation marks visible on the cup.

The stability of the foam is rated very good when no graduation is visible before 3 minutes have elapsed and poor when at least one graduation mark appears after 30 seconds.

The results obtained are tabulated below:

TABLE 1

| COMPOUND | A | B | C | D | E | F | G |
|---|---|---|---|---|---|---|---|
| Density g/cm$^3$ | 0.1 | 0.135 | 0.142 | 0.12 | 0.148 | 1.112 | 0.154 |
| Graduations visible after | | | | | | | |
| 30 sec | 0 | 0 | 0 | 7 | 3 | 7 | 5 |
| 45 sec | 0 | 0 | 0 | 10 | 7 | 9 | 7 |
| 1 min | 0 | 0 | 0 | 10 | 10 | 10 | 8 |
| 1.5 min | 0 | 0 | 0 | 10 | 10 | 10 | 10 |
| 2 min | 0 | 0 | 0 | 10 | 10 | 10 | 10 |
| 3 min | 0 | 0 | 1 | 10 | 10 | 10 | 10 |

As shown by the results obtained, there is no significant difference in the densities of the foams obtained, except for compound F, but as far as stability is concerned, it can be seen that the foams obtained with compounds A, B and C are particularly stable over time, which is not the case with the foams obtained with reference compounds D to G.

Examples of methods of preparation of compounds with general formula (I) will now be given for purposes of illustration, with no limitative nature, as well as a few examples of anhydrous cosmetic compositions in the aerosol form.

EXAMPLE I

Preparation of N-carbohexadecyloxy-11-aminoundecanoic acid (Formula I) in which R=H and $R_1C_{10}H_{33}$)

40.2 g of 11-aminoundecanoic acid (0.2 mole) are dissolved in a mixture of 450 ml acetone and 200 ml of a 1 N sodium hydroxide solution. Then, simultaneously, 60.9 g of hexadecyl chloroformate (0.2 mole) and 200 ml of a 1 N sodium hydroxide solution are added. A white precipitate appears gradually in the reaction medium, which is left to agitate for 5 hours. The reaction mixture is then filtered and the white precipitate obtained is rinsed with water. The alkaline salt obtained is centrifuged under vacuum, then dissolved and acidified while hot in 650 ml of acetic acid. Upon return to room temperature, a white precipitate appears which is filtered and washed with acetone.

The acid obtained is dried under vacuum at 40° C. to constant weight: >79 g (yield≧85%).

Melting point: 100° C.±1° C.

The $^{13}$C NMR spectrum conforms to the expected structure. IR spectrum: 1538 cm$^{-1}$ and 1679 cm$^{-1}$ (carbamate). Percent analysis: $C_{28}H_{55}NO_4$

| | C % | H % | N % | O % |
|---|---|---|---|---|
| Calc. | 71.59 | 11.80 | 2.98 | 13.62 |
| Found | 71.40 | 11.84 | 2.93 | 13.68 |

EXAMPLE II

Preparation of N-carbodecyloxy-11-aminoundecanoic acid (Formula 1 in which R=H and R=$C_{10}H_{21}$).

Using the same method as described above in Example I, and using 44.1 g of decyl chloroformate, 61 g of white crystals are obtained (yield =80%). Melting point =91° C. The $^1$H NMR spectrum conforms to the expected structure. IR spectrum: 1679 cm$^{-1}$ and 1535 cm$^{-1}$ (carbamate).

EXAMPLE III

Preparation of hexadecyl N-carbohexadecyloxy-11-aminoundecanoate (Formula I wherein R=$C_{16}H_{33}$ and $R_1$=$C_{16}H_{33}$)

(i) To 5 g of N-carbohexadecyloxy-11-aminoundecanoic acid obtained in Example 1 above, 2.7 g of hexadecanol, 300 mg of p-toluenesulfonic acid, and 120 ml of toluene are added. Dehydration is effected by azeotropic entrainment for 16 hours; then the reaction medium is evaporated to dryness under vacuum.

The white precipitate obtained is chromatographed on a silica column (eluent: methylene chloride).

After evaporation of the elution solvent under vacuum, 5.9 g of pure white crystals are recovered (yield −80%). Melting point =76° C. The $^{13}$C NMR spectrum conforms to the expected structure. IR spectrum: 1730 cm$^{-1}$ (ester) 1685 cm$^{-1}$ and 1536 cm$^{-1}$ (carbamate). Percent analysis: $C_{44}H_{87}NO_4$

|  | C % | H % | N % | O % |
| --- | --- | --- | --- | --- |
| Calc. | 76.13 | 12.63 | 2.02 | 9.22 |
| Found | 75.55 | 12.75 | 2.06 | 9.76 |

(ii) To 5 g of sodium carboxylate obtained as an intermediate in Example I, 3.4 g of 1-bromohexadecane in 100 ml of acetonitrile is added. After 8 hours' refluxing, the reaction medium is evaporated to dryness. The white precipitate obtained is chromatographed on a silica column (eluent: methylene chloride).

After evaporation of the elution solvent under vacuum, 4.6 g (yield: 65%) of pure white crystals identical to those obtained above in (i) are recovered.

EXAMPLES OF AEROSOL COMPOSITIONS

EXAMPLE 1

According to the invention, an aerosol foam for makeup removal is prepared by first mixing the following ingredients:

| | |
| --- | --- |
| Sorbitan oleate | 3.0% |
| Sorbitan oleate ethoxylated with 40 moles of ethylene oxide | 2.0% |
| Sorbitan trioleate ethoxylated with 20 moles of ethylene oxide | 7.0% |
| Isopropyl myristate | 20.0% |
| Liquid paraffin | 67.5% |
| Hexadecyl N-carbohexadecyloxy-11-aminoundecanoate | 0.2% |
| Fragrance | 0.3% |

Next, 95% of the composition obtained is placed in an aerosol container then, when the container has been closed, it is pressurized with 5% 1,1-difluoroethane as propellant.

A light foam with very good stability over time (greater than 4 min) is obtained.

EXAMPLE 2

According to the invention, an aerosol foam for makeup removal is prepared by first mixing the following ingredients:

| | |
| --- | --- |
| Sorbitan oleate ethoxylated with 40 moles of ethylene oxide | 6.0% |
| Sorbitan trioleate ethoxylated with 20 moles of ethylene oxide | 12.0% |
| Liquid paraffin | 51.5% |
| Hexadecyl N-carbohexadecyloxy-11-aminoundecanoate | 5.0% |
| Fragrance | 0.5% |
| Egg yolk lecithin | 5.0% |
| Sunflower seed oil | 20.0% |

Next, 95% of the composition obtained is placed in an aerosol container and, once the container has been closed, it is pressurized with the aid of 5%, 1,1-difluoroethane as propellant.

The foam obtained is compact, tight, and fine, It is very pleasant in application and is easily eliminated when water is applied to the face.

EXAMPLE 3

According to the invention, as aerosol foam for makeup removal is prepared by first mixing the following ingredients:

| | |
| --- | --- |
| Ethoxylated sorbitan oleate | 3.0% |
| Sorbitan trioleate | 4.0% |
| 2-Octyldodecanol | 20.0% |
| Isopropyl myristate | 20.0% |
| N-carbohexadecyloxy-11-aminoundecanoic acid | 1.5% |
| Fragrance | 0.3% |
| Liquid paraffin | 51.2% |

Next, 94% of the composition obtained is placed in an aerosol container and, once the container has been closed, it is pressurized with the aid of 6% carbon dioxide as propellant.

In this example, N-carbohexadecyloxy-11-aminooundecanoic acid can be replaced by the same quantity of N-carbodecyloxy-11-aminoundecanoic acid.

EXAMPLE 4

According to the invention, as aerosol foam for makeup removal is prepared by first mixing the following ingredients:

| | |
| --- | --- |
| Jojoba oil | 10% |
| Egg yolk lecithin | 10% |
| Hexadecyl N-carbohexadecyloxy-11-aminoundecanoate | 20% |
| Fragrance | 0.3% |
| Liquid paraffin | 57.7% |

Next, 90% of the composition obtained is placed in an aerosol container and, once the container has been closed, it is pressurized with the aid of 10% butane.

EXAMPLE 5

According to the invention an aerosol foam for makeup removal is prepared by first mixing the following ingredients:

| | |
|---|---|
| Liquid paraffin | 20% |
| 2-octyldodecanol | 30% |
| Sorbitan tetraoleate | 20% |
| Hexadecyl N-carbohexadecyloxy-11-aminoundecanoate | 1% |
| Fragrance | 0.2% |
| Isopropyl myristate | 28.8% |

Next, 92% of the composition obtained is placed in an aerosol container and, once the container has been closed, it is pressurized with the aid of 8% 1,1-difluoroethane.

We claim;

1. An anhydrous cosmetic aerosol composition capable of forming foam, comprising a propellant present in a concentration between 1 and 20% by weight relative to the total weight of the composition and an oil phase containing 20-99.95% by weight relative to the total weight of said oil phase of at least one cosmetic oil or a mixture of a cosmetic oil and a fatty substance and 0.05-20% by weight relative to the total weight of said phase of at least one foaming agent having the following formula:

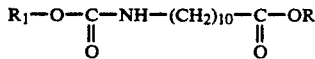

wherein:

R represents a hydrogen atom or an alkyl radical having 14 to 20 carbon atoms, and $R_1$ represents an alkyl radical having 8 to 18 carbon atoms.

2. Composition according to claim 1, wherein R represents an alkyl radical having 16 to 18 carbon atoms and $R_1$ represents an alkyl radical having 10 to 16 carbon atoms.

3. Composition according to claim 1, wherein the alkyl radical having 14 to 20 carbon atoms is selected from the group consisting of tetradecyl, hexadecyl, and octadecyl.

4. Composition according to claim 1, wherein the alkyl radical having 8 to 18 carbon atoms is selected from the group consisting of octyl, decyl, dodecyl, tetradecyl, hexadecyl, 2-hexyldecyl, and isostearyl.

5. Composition according to claim 1, wherein the foaming agent is selected from the group consisting of: N-carbohexadecyloxy-11-aminoundecanoic acid N-carbodecyloxy-11-aminoundecanoic acid hexadecyl N-carbohexadecyloxy-11-aminoundecanoate, octadecyl N-carbohexadecyloxy-11-aminoundecanoate, and hexadecyl N-carbohexadecyloxy-11-aminoundecanoate.

6. Composition according to claim 1, wherein the oily phase contains 25 to 85% of at least one oil or a mixture of an oil and a fatty substance relative to the total weight of said phase.

7. Composition according to claim 1, wherein the foaming agent is present in the oily phase in a proportion of between 0.2 and 5 wt.% relative to the total weight of said phase.

8. Composition according to claim 1, wherein the oily phase also contains at least one oil-soluble nonionic surfactant present in a concentration of between 5 and 60% by weight relative to the total weight of the oily phase.

9. Composition according to claim 1, wherein the propellant is present in a concentration between 3 and 15 wt.% relative to the total weight of the composition.

10. Composition according to claim 1, wherein the propellant is selected from the group consisting of carbon dioxide, nitrous oxide, propane, butanes, pentane, isopentane, neopentane, 1,1-difluoroethane, dichlorotetrafluoroethane, monochlorodifluoromethane, dichlorodifluoromethane, monochlorodifluoroethane, and mixtures thereof.

* * * * *